(12) United States Patent
Hungerford et al.

(10) Patent No.: US 12,151,079 B2
(45) Date of Patent: *Nov. 26, 2024

(54) INFUSION PUMP AND METHOD TO PREVENT TITRATION ERRORS IN INFUSION THERAPIES

(71) Applicants: BAXTER INTERNATIONAL INC., Deerfield, IL (US); BAXTER HEALTHCARE S.A., Glattpark (CH)

(72) Inventors: Roger L. Hungerford, Medina, NY (US); Curt Matthew Allen, Medina, NY (US)

(73) Assignees: BAXTER INTERNATIONAL INC., Deerfield, IL (US); BAXTER HEALTHCARE S.A., Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/598,926

(22) Filed: Oct. 10, 2019

(65) Prior Publication Data
US 2020/0038582 A1 Feb. 6, 2020

Related U.S. Application Data

(63) Continuation of application No. 12/322,898, filed on Feb. 9, 2009, now Pat. No. 10,441,710.

(51) Int. Cl.
*A61M 5/14* (2006.01)
*A61M 5/168* (2006.01)

(52) U.S. Cl.
CPC ...... *A61M 5/1407* (2013.01); *A61M 5/16804* (2013.01); *A61M 5/1414* (2013.01); *A61M 2205/18* (2013.01); *A61M 2205/50* (2013.01)

(58) Field of Classification Search
None
See application file for complete search history.

(56) References Cited

U.S. PATENT DOCUMENTS

| 4,469,481 A | 9/1984 | Kobayashi |
| 4,898,578 A | 2/1990 | Rubalcaba, Jr. |

(Continued)

FOREIGN PATENT DOCUMENTS

| WO | WO-2007133279 A2 * | 11/2007 | ........... A61B 5/0002 |
| WO | WO-2008019016 A2 * | 2/2008 | ............ A61M 5/142 |

OTHER PUBLICATIONS

Arends, Rosalinda Helena Gerardus Petronella. "Pharmacokinetics and Pharmacodynamics of Opioid Analgesics." Order No. 9907874 University of Washington, 1998. Ann Arbor: ProQuest. Web. Mar. 28, 2024. (Year: 1998).*

(Continued)

*Primary Examiner* — Lena Najarian
(74) *Attorney, Agent, or Firm* — Greer, Burns & Crain, Ltd (57) ABSTRACT

An infusion pump including an interface unit for receiving first data for a first infusion regimen for a medication, the first regimen including a first unit of measure in which the first regimen is executed and after receipt of the first data, second data for a second infusion regimen for the medication, the second regimen including a second unit of measure in which the second regimen is executed. The pump also includes a processor for comparing the first and second units of measure. In one embodiment, the pump includes a graphical user interface, and the processor identifies a difference between the first and second units of measure; generates, using the processor, a warning message; and displays the message on the graphical user interface. In another embodiment, the processor holds in abeyance initiation of the second infusion regimen in response to identifying the difference between the units of measure.

6 Claims, 6 Drawing Sheets

(56) References Cited

U.S. PATENT DOCUMENTS

| | | |
|---|---|---|
| 5,733,259 A | 3/1998 | Valcke et al. |
| 5,772,635 A | 6/1998 | Dastur et al. |
| 6,269,340 B1 | 7/2001 | Ford et al. |
| 6,985,870 B2 | 1/2006 | Martucci et al. |
| 7,229,430 B2 | 6/2007 | Hickle et al. |
| 7,895,053 B2 * | 2/2011 | Holland ............ G16H 20/17 |
| | | 600/300 |
| 2002/0038392 A1 | 3/2002 | De La Huerga |
| 2002/0043951 A1 | 4/2002 | Moberg |
| 2002/0183683 A1 | 12/2002 | Lerner |
| 2003/0135087 A1 | 7/2003 | Hickle et al. |
| 2003/0144878 A1 | 7/2003 | Wilkes et al. |
| 2004/0167804 A1 * | 8/2004 | Simpson ............ A61B 5/4839 |
| | | 705/3 |
| 2004/0172302 A1 | 9/2004 | Martucci et al. |
| 2004/0225252 A1 * | 11/2004 | Gillespie, Jr. ....... A61M 5/1456 |
| | | 417/53 |
| 2005/0145009 A1 | 7/2005 | Vanderveen et al. |
| 2005/0177096 A1 | 8/2005 | Bollish et al. |
| 2006/0047538 A1 | 3/2006 | Condurso et al. |
| 2006/0129357 A1 | 6/2006 | Francis et al. |
| 2006/0167722 A1 | 7/2006 | MRF Struys et al. |
| 2006/0200369 A1 | 9/2006 | Batch et al. |
| 2006/0229551 A1 | 10/2006 | Martinez et al. |
| 2006/0258985 A1 | 11/2006 | Russell |
| 2007/0124002 A1 * | 5/2007 | Estes ................ A61M 5/172 |
| | | 700/20 |
| 2007/0210157 A1 | 9/2007 | Miller |
| 2007/0233521 A1 | 10/2007 | Wehba et al. |
| 2007/0257788 A1 | 11/2007 | Carlson et al. |
| 2008/0033361 A1 | 2/2008 | Evans et al. |
| 2008/0071251 A1 | 3/2008 | Moubayed et al. |
| 2008/0126969 A1 * | 5/2008 | Blomquist ........... A61M 5/142 |
| | | 715/771 |
| 2009/0153058 A1 | 6/2009 | Feng et al. |

OTHER PUBLICATIONS

Husch et al., "Insights from the Sharp End of Intravenous Medication Errors: Implications for Infusion Pump Technology", Quality and Safety in Health Care (2005), 14(2), pp. 80-86.

* cited by examiner

INFUSION PUMP AND METHOD TO PREVENT TITRATION ERRORS IN INFUSION THERAPIES

RELATED APPLICATION

This application is a continuation application of and claims 35 USC 120 priority to U.S. patent application Ser. No. 12/322,898 filed Feb. 9, 2009, which is incorporated herein by reference.

FIELD OF THE INVENTION

The invention relates generally to an infusion pump with functionality to address possible problems related to a secondary infusion configuration and units of measure for an infusion regimen.

BACKGROUND

Prior art infusion pumps teach unqueried changes in units of measure for infusion regimens.

SUMMARY

The invention broadly comprises an infusion pump for preventing titration errors in infusion therapies, including an interface unit for receiving first data for a first infusion regimen for a medication, the first regimen including a first unit of measure in which the first regimen is executed and after receipt of the first data, second data for a second infusion regimen for the medication, the second regimen including a second unit of measure in which the second regimen is executed. The pump also includes a processor for comparing the first and second units of measure.

In one embodiment, the pump includes a graphical user interface, and the processor is for identifying a difference between the first and second units of measure; generating, using the processor, a warning message regarding the difference; and displaying the warning message on the graphical user interface. In another embodiment, the processor is for holding in abeyance initiation of the second infusion regimen in response to identifying the difference between the first and second units of measure. In a further embodiment, the processor is for operating the pump according to the first regimen prior to receipt of the second data.

In one embodiment, the processor is for determining that the first and second units of measure are the same and enabling initiation of the second infusion regimen responsive to the determination that the first and second units of measure are the same.

The invention also broadly comprises an infusion pump for preventing titration errors in infusion therapies, including: an interface unit, including a graphical user interface (GUI), for receiving first and second data for first and second infusion regimens for first and second medications, respectively. Respective tubing from first and second containers, containing the first and second medications, respectively, is connected to a tube passing through the pump. The second medication exerts a greater gravitational head pressure than the first medication. The pump also includes a processor for generating a query regarding inclusion, in the second data, of a volume of the second medication. The GUI is for displaying the query.

In one embodiment, the query includes a request to confirm, via the GUI, the volume of the second medication and the processor is holding in abeyance initiation of the second regimen after receipt of the first and second data. The GUI is for receiving volume data including information regarding the volume of the second medication, and the processor is for enabling initiation of the second regimen responsive to receiving the volume data.

The invention further broadly comprises an infusion pump for preventing titration errors in infusion therapies, including: an interface unit, with a graphical user interface (GUI), for receiving first data for an infusion regimen for a medication; and a processor for initiating the infusion regimen. The GUI is for displaying, at a specified time with respect to initiation of the infusion regimen, a message regarding a desired action. In one embodiment, the first data include the message and the specified time. In another embodiment, the interface is for receiving, separate from the first data, second data including the message and the specified time.

The invention broadly comprises computer-based methods to prevent titration errors in infusion therapies.

It is a general object of the present invention to provide a pump and method to prevent titration errors in infusion therapies due to changes in units of measure or in primary/secondary configurations.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
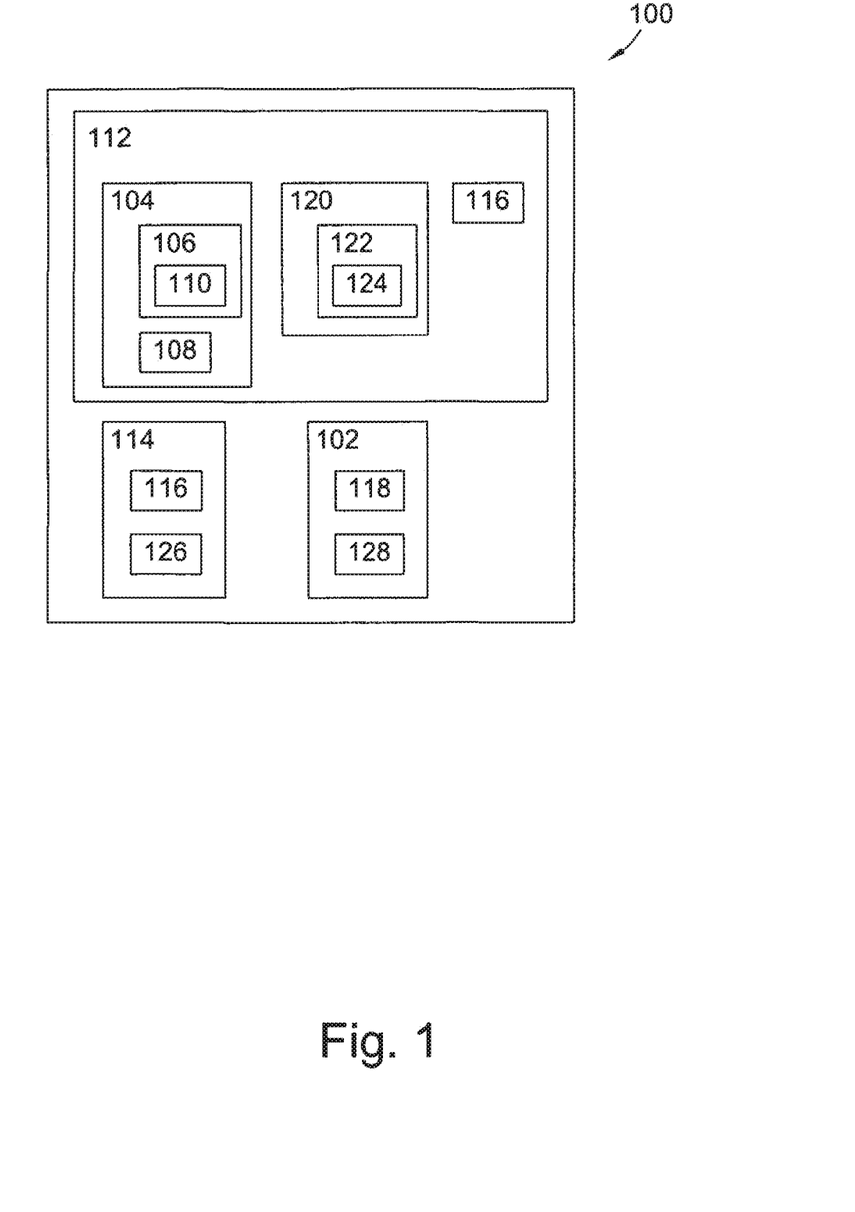
FIG. 1 is a prospective view of a present invention infusion pump for preventing titration errors in infusion therapies.

FIG. 1 is a block diagram of present invention infusion pump 100 for preventing titration errors in infusion therapies. The pump includes interface unit 102, arranged to receive, that is, for receiving, data 104 for infusion regimen 106 for medication 108, identified in data 104. Regimen 106 includes unit of measure 110 in which regimen 106 is executed. For example, measure 110 is the unit of measure in which medication 108 is to be infused. Data 104 is stored in memory element 112. In one embodiment, the interface element includes a graphical user interface (GUI) and processor 114 generates message 116 including a prompt to verify that regimen 106 is the desired regimen and transmits the message for display on the GUI. If applicable, the interface unit receives input 118, via the prompt and the GUI, confirming regimen 106 as the desired regimen for infusion of medication 108.

After receipt of data 104, the interface is for receiving data 120 for regimen 122 for medication 108. Regimen 122 includes unit of measure 124 in which regimen 122 is executed. Data 120 is stored in memory element 112. Processor 114 compares units of measure 110 and 124. Regimens 106 and 122 can be any regimens known in the art, units of measure 110 and 124 can be any units of measure known in the art, and medication 108 can be any infusible medication known in the art. In one embodiment, data 120 is received after regimen 106 has been initiated, that is, the infusion of medication 108 according to regimen 106 has been started and the infusion is to be modified according to regimen 122.

In one embodiment, the processor is for identifying a difference between units of measure 110 and 124. In another embodiment, if a difference between units of measure 110 and 124 is identified, the processor generates warning, or reminder, message 126 regarding the difference between the units of measure and holds the initiation of regimen 122 in abeyance. That is, the processor does not enable initiation of regimen 122 and the initiation cannot commence until further action by the processor. Any type of warning or reminder can be included in message 126, for example, an alert that the units of measure are different, a query as to whether the change in units of measure is intentional, or a reminder to carefully check remaining infusion parameters if the change is intentional. Message 126 is transmitted for display on the GUI. In another embodiment, message 126 includes a prompt, for example, to provide confirmation that the change in units of measure is known or intentional and that all infusion parameters have been properly adjusted. As applicable, confirmation input 128 is received via the GUI responsive to the prompt, and in response to receiving the confirmation input, the processor enables initiation of regimen 122. The regimen can be automatically initiated by the processor or the processor can initiate other steps, such as providing a prompt for display on the GUI to which a caregiver would respond to initiate the regimen, for example, a "start" icon. In a further embodiment, message 126 includes an advisement that regimen 122 must be re-entered using units 110. The processor does not enable initiation of regimen 122 until regimen 122 is re-entered in units 110.

In one embodiment, the processor determines that units of measure 110 and 124 are the same and enables initiation of regimen 122. The regimen can be automatically initiated by the processor or the processor can initiate other steps, such as providing a prompt for display on the GUI to which a caregiver would respond to initiate the regimen, for example, a "start" icon.

As an example, if a specific medication, for example, medication 108, is prescribed, for example, regimen 106, to be delivered in a specific unit of measure, for example, unit of measure 110 is mcg/kg/min, any changes to the delivery rate of medication 108 by pump 100, for example, regimen 122, also must be made in the same unit of measure to avoid errors, for example, errors associated with manually converting a desired amount of medication into mL/hr. That is, units 110 and 124 must be the same.

Medical institutions are striving to reduce medication errors, especially those associated with the use of an infusion pump. The typical goal of a medication error reduction system is to ensure the five rights of medication delivery: Right patient, Right medication, Right dose, Right time, and Right route. One error that can occur in the process of delivering medication to a patient is to initiate an infusion in a first unit of measure and then modify the infusion by changing to a different unit of measure without properly adjusting the remaining infusion parameters, for example, the infusion rate. Advantageously, pump 100 provides a means of addressing and preventing errors related to changes in units of measure.

Figure 2:
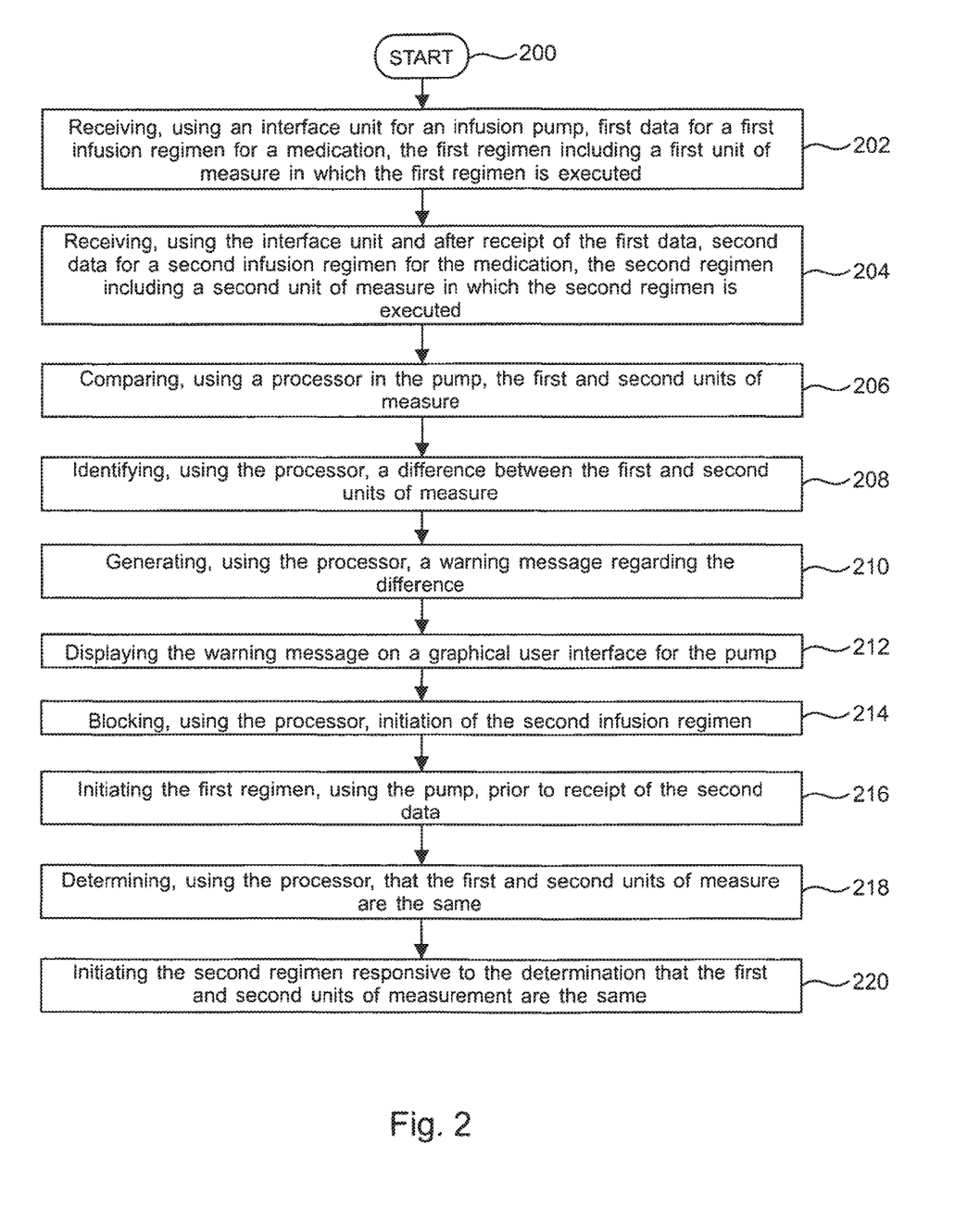
FIG. 2 is a flow chart of a present invention method to prevent titration errors in infusion therapies.

FIG. 2 is a flow chart illustrating a present invention computer-based method of preventing titration errors in infusion therapies. Although the method in FIG. 2 (and FIGS. 4 and 6 below) is depicted as a sequence of numbered steps for clarity, no order should be inferred from the numbering unless explicitly stated. The method starts at Step 200. Step 202 receives, using an interface unit for an infusion pump, first data for a first infusion regimen for a medication, the first regimen including a first unit of measure in which the first regimen is executed; step 204 receives, using the interface unit and after receipt of the first data, second data for a second infusion regimen for the medication, the second regimen including a second unit of measure in which the second regimen is executed; and step 206 compares, using a processor in the pump, the first and second units of measure.

In one embodiment, step 208 identifies, using the processor, a difference between the first and second units of measure; step 210 generates, using the processor, a warning message regarding the difference; and step 212 displays the warning message on a graphical user interface for the pump. In another embodiment, step 214 holds in abeyance, using the processor, initiation of the second infusion regimen. In a further embodiment, step 216 initiates the first regimen, using the processor, prior to receipt of the second data.

In one embodiment, step 218 determines, using the processor, that the first and second units of measure are the same; and step 220 initiates, using the processor, the second regimen responsive to the determination that the first and second units of measure are the same.

Figure 3:
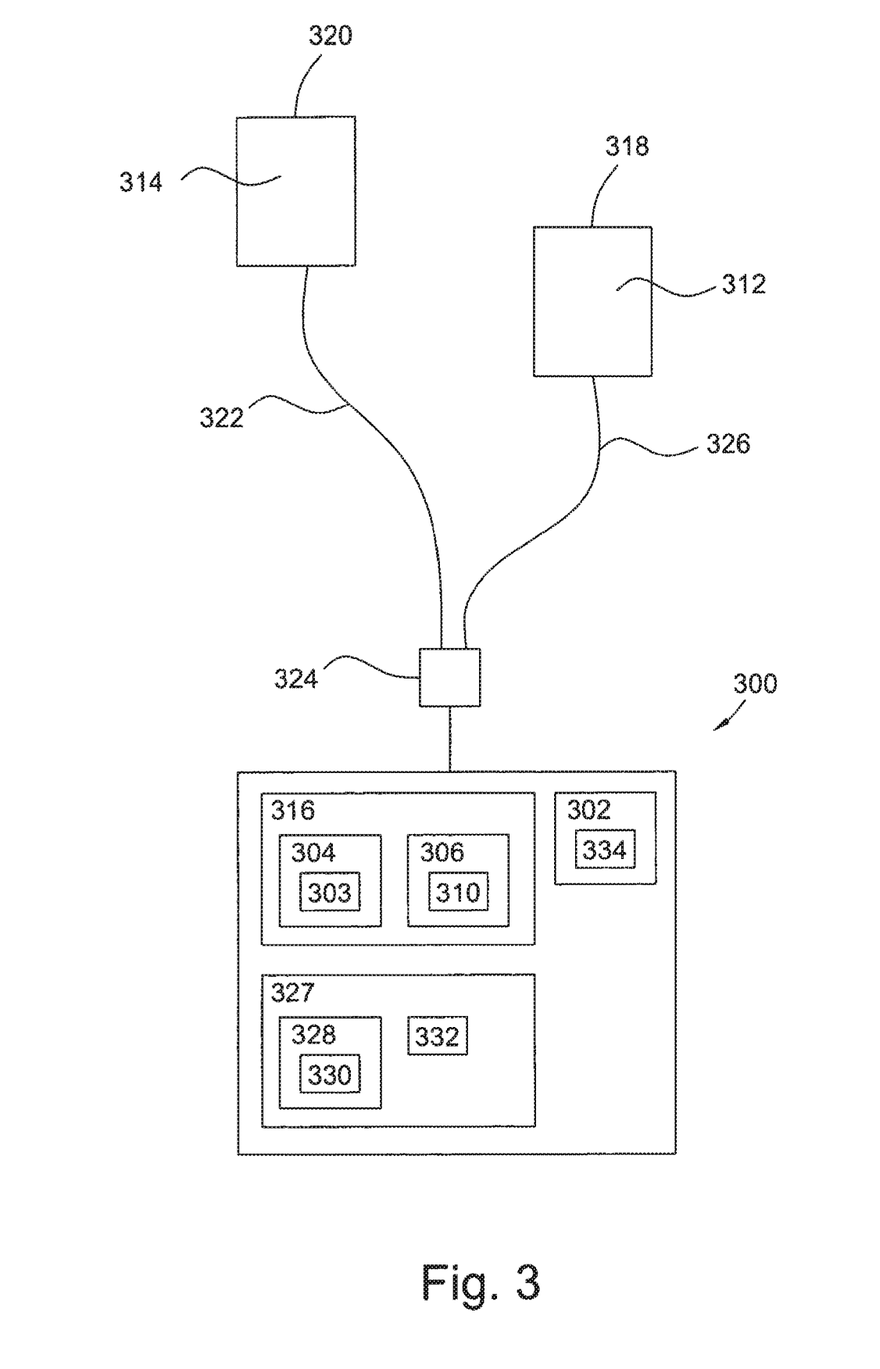
FIG. 3 is a prospective view of a present invention infusion pump for preventing titration errors in infusion therapies.

FIG. 3 is a block diagram of present invention infusion pump 300 for preventing titration errors in infusion therapies. The pump includes interface unit 302 for receiving data 304 and 306 for infusion regimens 308 and 310 for medications 312 and 314, respectively. Data 304 and 306 is stored in memory element 316. Medications 312 and 314 are disposed in primary and secondary containers 318 and 320, respectively. Containers 318 and 320 are arranged in a primary/secondary infusion configuration. For example, primary medication 312 is administrated in coordination with secondary medication 314. As is known in the art, in a primary/secondary configuration, the medication in the secondary container is infused before the medication in the primary container. The secondary container is hung higher than the primary container, for example, by at least 10 inches. As a result, medication 314 exerts a greater gravitational head pressure than medication 312. The primary/secondary infusion configuration can be any configuration known in the art.

Respective tubing from containers 318 and 320 are connected to a tube passing through the pump. Any such configuration known in the art can be used. In one embodiment, tubing 322 from the secondary container is connected to injection port 324 in tube 326 for container 318, which then is engaged with, for example, passes through pump 300. Typically tube 326 is part of a set (not shown) and the set can include a check valve to prevent fluid from the secondary back flowing into the primary bag. It should be understood that any primary/secondary tubing arrangement known in the art can be used. Utilizing the difference in head height and head pressure, medication 314 is delivered before medication 312. When container 320 is empty, delivery of medication 312 can commence.

Processor 327 generates query 328 regarding inclusion, in data 306, of a volume of medication 314. In one embodiment, the interface includes a graphical user interface (GUI) and query 328 is displayed on the GUI. In another embodiment, the query includes request 330 to confirm, via the GUI, the volume of medication 314. In a further embodiment the processor holds the initiation of regimen 310 in abeyance after receipt of data 304 and 306. That is, the processor does not enable initiation of regimen 310, for example, infusion of medication 314, and the initiation cannot commence until further action by the processor. The processor generates prompt 332 requesting the volume of medication 314. The prompt is displayed on the GUI and in response to receipt, in the GUI, of input 334, including the volume of medication 314, the processor enables initiation of regimen 310. The regimen can be automatically initiated by the processor or the processor can initiate other steps, such as providing a prompt for display on the GUI to which a caregiver would respond to initiate the regimen, for example, a "start" icon.

Medical institutions are striving to reduce medication errors, especially those associated with the use of an infusion pump. The typical goal of a medication error reduction system is to ensure the five rights of medication delivery: Right patient, Right medication, Right dose, Right time, and Right route. One error that can occur in the process of delivering medication to a patient in a primary/secondary configuration is related to the flow rate for the primary medication. Since the flow rate for a secondary infusion is often different from that of the primary infusion, it is important to make sure the total volume of medication to be delivered from the secondary container is correctly entered. For example, a secondary container volume is 100 mL; secondary flow rate is 100 mL/hr; and primary flow rate is 20 mL/hr. If the volume to be infused for the secondary container is programmed as 125 mL in the pump, the medication in the secondary container will be delivered at the correct rate. However primary medication will be delivered at 100 mL/hr for the next 25 mL, instead of the correct rate of 20 mL/hr. That is, the primary medication will be delivered five times faster than the correct rate. This may have significant negative consequence, especially when the primary infusion contains high-alert drug such as insulin. Advantageously, pump 100 provides a means of ensuring that the volume of the secondary container is correctly entered.

Figure 4:
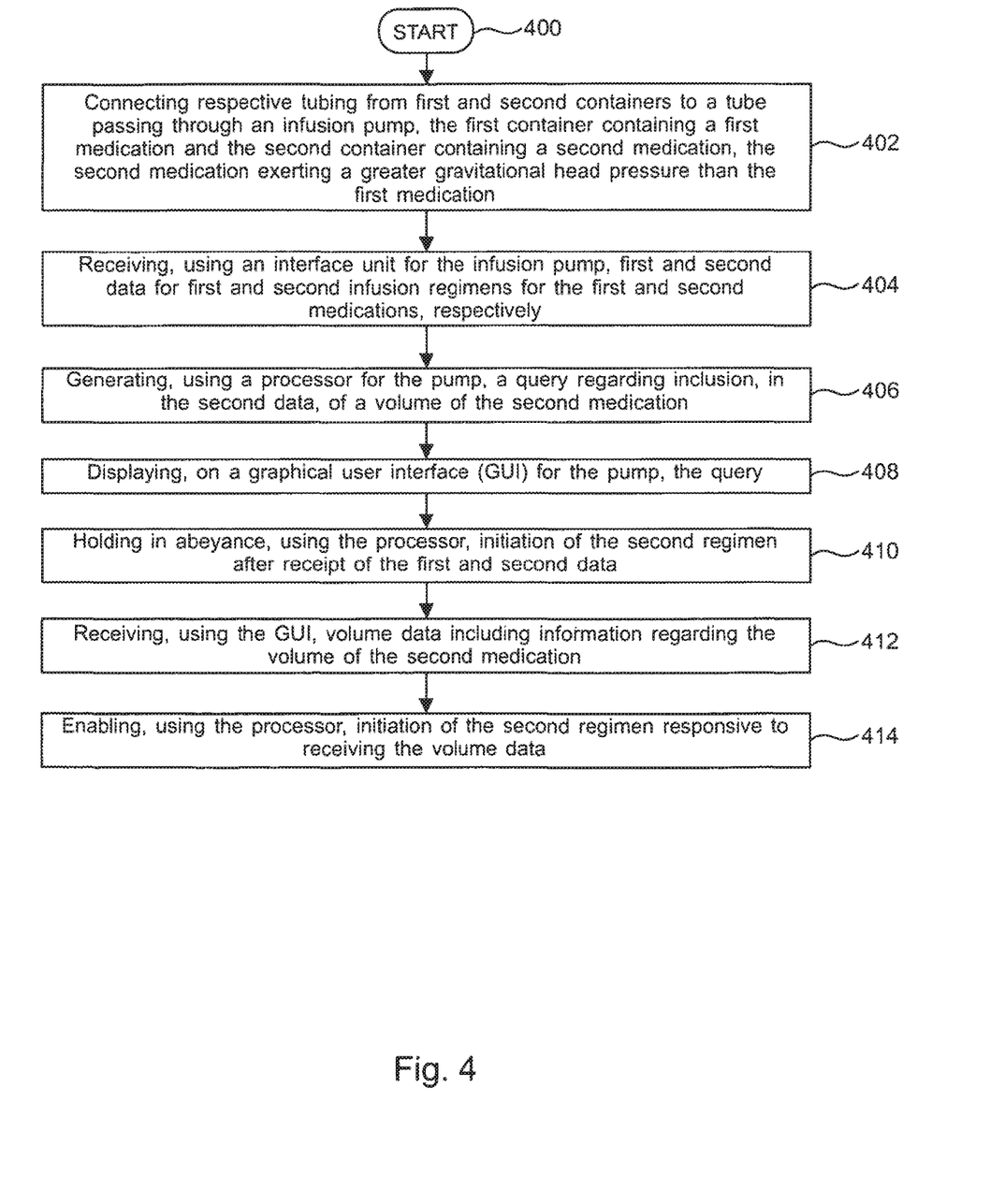
FIG. 4 is a flow chart of a present invention method to prevent titration errors in infusion therapies.

FIG. 4 is a flow chart illustrating a present invention computer-based method of preventing titration errors in infusion therapies. Although the method in FIG. 4 is depicted as a sequence of numbered steps for clarity, no order should be inferred from the numbering unless explicitly stated. The method starts at Step 400. Step 402 connects respective tubing from first and second containers to a tube passing through an infusion pump, the first container containing a first medication and the second container containing a second medication, the second medication exerting a greater gravitational head pressure than the first medication; step 404 receives, using an interface unit for the infusion pump, first and second data for first and second infusion regimens for the first and second medications, respectively; step 406 generates, using a processor for the pump, a query regarding inclusion, in the second data, of a volume of the second medication; and step 408 displays, on a graphical user interface (GUI) for the pump, the query.

In one embodiment, the query includes a request to confirm, via the GUI, the volume of the second medication and step 410 holds in abeyance, using the processor, initiation of the second regimen after receipt of the first and second data; step 412 receives, using the GUI, volume data including information regarding the volume of the second medication; and step 414 enables, using the processor, initiation of the second regimen responsive to receiving the volume data.

Figure 5:
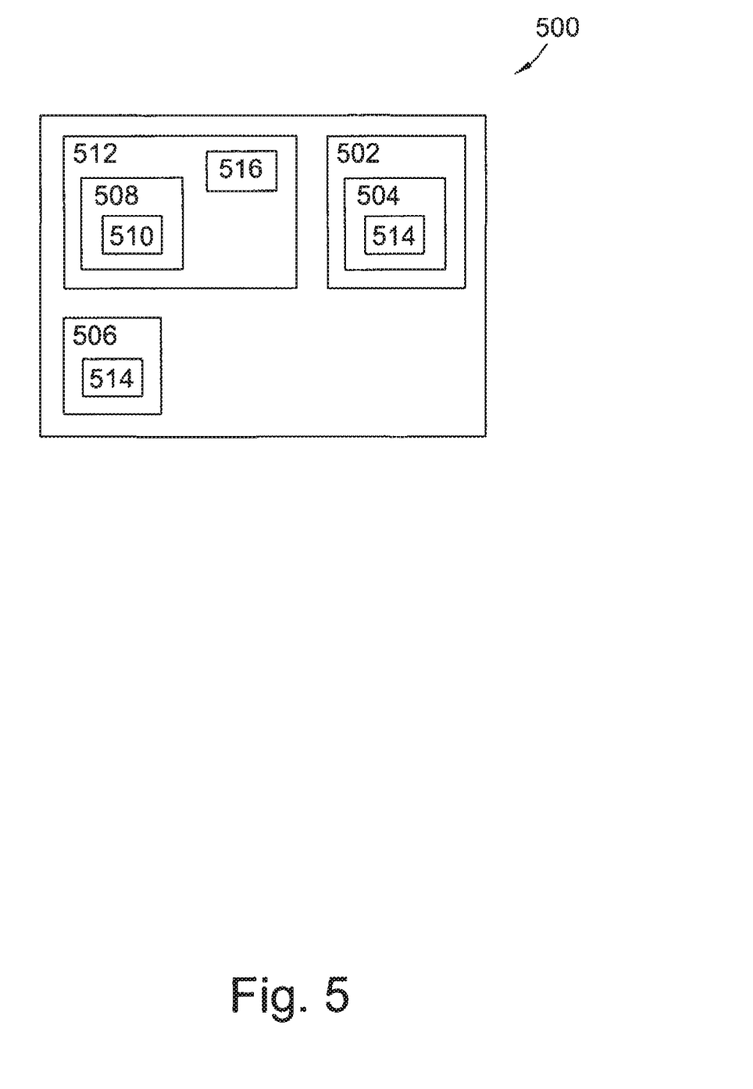
FIG. 5 is a prospective view of a present invention infusion pump for preventing titration errors in infusion therapies; and, FIG. 6 is a flow chart of a present invention method to prevent titration errors in infusion therapies.

FIG. 5 is a block diagram of present invention infusion pump 500 for preventing titration errors in infusion therapies. The pump includes interface unit 502 with graphical user interface (GUI) 504, and processor 506. The interface unit is for receiving data 508 for infusion regimen 510 for a medication. The data is stored in memory element 512. The processor initiates the infusion regimen and generates message 514 regarding a desired action. The GUI displays, at a specified time with respect to initiation of the infusion regimen, the message. The display can include any combination of audio and visual presentations. In one embodiment, data 508 includes the content of the message and the specified time. In another embodiment, the interface receives, separate from data 508, data 516 including the content of the message and the specified time. Data 516 is stored in the memory element.

Advantageously, pump 500 enables display of communications, such as reminders regarding tasks that need to be performed at specific times or intervals, without the use of additional equipment and in a readily accessible format. For example, the desire action can be a call back. In many infusion therapies, a nurse wants to be informed at certain important junctures during the therapy. For example, in secondary infusion, a nurse may want to be called back after the secondary infusion is completed. In other scenarios, a nurse may want to be reminded after a certain time to measure patient glucose level or to draw blood for a blood test. Advantageously, pump 500 provides such reminder or call-back functionality.

Figure 6:
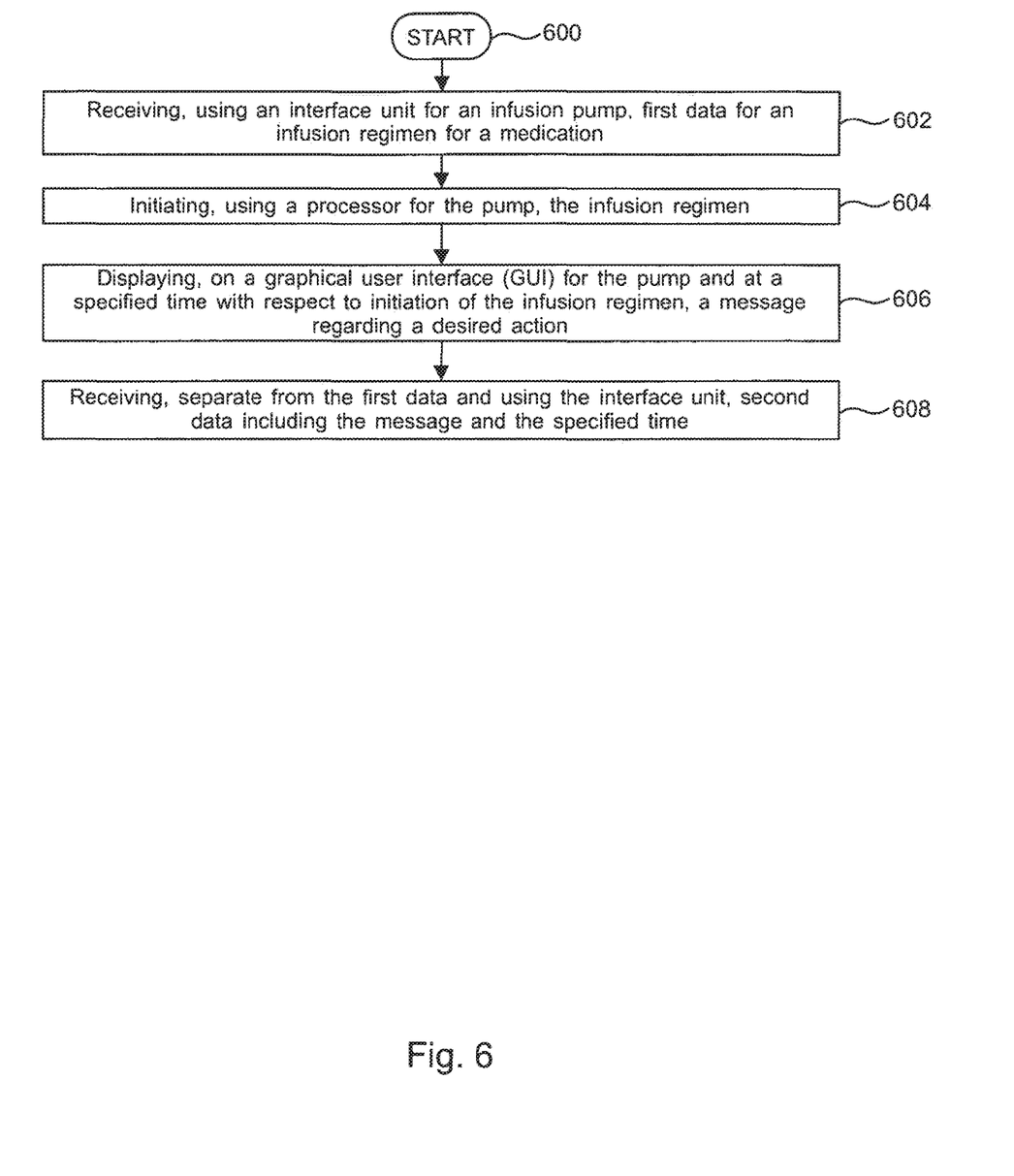

FIG. 6 is a flow chart illustrating a present invention computer-based method of preventing titration errors in infusion therapies. Although the method in FIG. 6 is depicted as a sequence of numbered steps for clarity, no order should be inferred from the numbering unless explicitly stated. The method starts at Step 600. Step 602 receives, using an interface unit for an infusion pump, first data for an infusion regimen for a medication; step 604 initiates, using a processor for the pump, the infusion regimen; and step 606 displays, on a graphical user interface (GUI) for the pump and at a specified time with respect to initiation of the infusion regimen, a message regarding a desired action. In one embodiment, the first data include the message and the specified time. In another embodiment, step 608 receives, separate from the first data and using the interface unit, second data including the message and the specified time.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed is:

1. A method for operating an infusion pump, the infusion pump including an interface unit having a display, the interface unit including a graphical user interface, the method comprising:
  directly receiving, by the graphical user interface of the interface unit, a first input from a user including first data for a first infusion regimen for a medication, the first data including a first delivery rate in which the first regimen is executed, the first delivery rate including a first unit of measure;
  storing the first data in a memory element of the infusion pump;
  initiating, by a processor in the pump, operation of the pump to infuse the medication according to the first regimen including the first delivery rate;
  the pump operating in response to said initiating to deliver the medication to a patient according to the first regimen including the first delivery rate;
  directly receiving, by the graphical user interface of the interface unit, after receipt of the first data and after said initiating operation of the pump according to the first regimen, a second input from the user or a different user including second data for a second infusion regimen for the medication that is infused by the pump during said operating, the second infusion regimen modifying the first regimen, the second data including a second delivery rate in which the second regimen is executed, the second delivery rate including a second unit of measure;
  directly comparing, by the processor in the pump, the second unit of measure input within the said second data via the graphical user interface of the interface unit to the first unit of measure input within the first data received via the graphical user interface of the interface unit;
  detecting, by the processor in the pump, an error in the second delivery rate input within the said second data based solely on said comparing, the detected error comprising a difference between the first unit of measure in the first input delivery rate and the second unit of measure in the second input delivery rate;
  in response to said detecting an error:
    automatically holding, using the processor in the pump, the second infusion regimen in abeyance;
    generating an alert message; and
    displaying said generated alert on the display of the interface unit.

2. The method of claim 1, further comprising:
  receiving third input data in response to said generated alert via the graphical user interface of the interface unit, said third input data including a confirmation of said second delivery rate; and
  based on said received third input data, initiating, by the processor, operation of the pump to infuse the medication according to the second regimen including the second delivery rate;
  the pump operating in response to said initiating to deliver the medication to the patient according to the second regimen including the second delivery rate.

3. The method of claim 1, further comprising:
  receiving third input data in response to said generated alert via the graphical user interface of the interface unit, said third input data including a reentered second delivery rate; and
  based on said third input data, initiating, by the processor, the pump to infuse the medication according to the second regimen including the reentered second delivery rate;
  the pump operating in response to said initiating to deliver the medication to the patient according to the second regimen including the reentered second delivery rate.

4. An apparatus comprising:
  a pump configured to deliver medication to a patient from a container via tubing engaged with the pump, the pump including an interface unit having a display;
  a memory element;
  the interface unit including a graphical user interface configured to directly receive:
    a first input from a user including first data for a first infusion regimen for a medication, the received first data including a first delivery rate in which the first regimen is executed, the first delivery rate including a first unit of measure; and,
    a second input from the user or a different user including second data for a second infusion regimen for the same medication as for the first infusion regimen, the second regimen modifying the first regimen, the second data including a second delivery rate in which the second regimen is executed, the second delivery rate including a second unit of measure; and,
  a processor in the pump configured for:
    initiating operation of the pump to infuse the medication according to the first regimen including the first delivery rate received via the graphical user interface, wherein the pump operates in response to said initiating to deliver the medication to the patient according to the first regimen including the first delivery rate;
    after receipt of the second data, directly comparing the second unit of measure input within the second data received via the graphical user interface to the first unit of measure input within the first data received via the graphical user interface, wherein the second input including the second data is received via the graphical user interface after said initiating operation of the pump;
    detecting an error in the second delivery rate input within the second data solely based on said comparing, the detected error comprising a difference between the first unit of measure in the first input delivery rate and the second unit of measure in the second input delivery rate; and
    in response to said detecting an error:
      automatically holding, by the processor in the pump, the second infusion regimen in abeyance;

generating an alert message; and displaying said generated alert on the display of the interface unit.

5. The apparatus of claim 4, wherein said processor is further configured for:

receiving a third input in response to said generated alert via the graphical user interface, said third input including a confirmation of said second delivery rate; and in response to said received third input, initiating operation, by the processor, of the pump to infuse the medication according to the second regimen including the second delivery rate, wherein the pump operates in response to said initiating to deliver the medication to the patient according to the second regimen including the second delivery rate.

6. The apparatus of claim 4, wherein said processor is further configured for:

receiving a third input in response to said generated alert via the graphical user interface, said third input including a reentered second delivery rate; and in response to said third input initiating operation, by the processor, of the pump to infuse the medication according to the second regimen including the reentered second delivery rate, wherein the pump operates in response to said initiating to deliver the medication to the patient according to the second regimen including the reentered second delivery rate.

* * * * *